United States Patent [19]

Jolly

[11] Patent Number: Plant 7,340

[45] Date of Patent: Oct. 2, 1990

[54] ROSE PLANT NAMED 'TIPPER'

[76] Inventor: Marie Jolly, Gregg Neck Rd., Galena, Md. 21635

[21] Appl. No.: 388,698

[22] Filed: Aug. 2, 1989

[51] Int. Cl.[5] ..... A01H 5/00

[52] U.S. Cl. ..... Plt./9

[58] Field of Search ..... Plt. 7, 9

*Primary Examiner*—James R. Feyrer

[57] ABSTRACT

A new and distinct variety of rose plant of the miniature rose class, which was originated by my crossing Chris Jolly as a seed parent and Chattem Centennial as the pollen parent; characterized by it's strong upright growing habit, well formed coral pink blooms which do not fade or lose their strong substance when cut.

1 Drawing Sheet

1

The present invention relates to a new and distinct variety of rose plant of the miniature rose class, which was originated by my crossing as seed parent the rose known as "Chris Jolly" and the rose known as "Chattem Centennial" as pollen parent.

Among the novel characteristics possessed by this new variety which distinguishes it from other varieties of which I am aware are:

1. The bud is exhibition type, the bloom is high centered 1½" in diameter, full blown and retaining a clear coral pink color in all stages of opening.

2. The blooming habit of this miniature is singly, and an excellent repeater being therefore an attractive rose for the garden or cut flower market.

3. Vigorous upright growing plant that reaches a height of 40–45 cms. having medium green foliage with strong, straight canes.

Asexual reproduction by budding of this variety as performed in Kent County, Md. shows that the foregoing and other distinguishing characteristics come true to form and are established and transmitted through succeeding propagation.

The color of this new and improved variety developed by me is an unusual coral pink that holds it color from bud to mature bloom and also upon aging. The flower has ovid petals, recurling to a flat open flower.

The accompanying drawing shows typical specimens of the vegetative growth and flowers of this new variety depicted in color as nearly true as it is reasonably possible to make the same in a color illustration of this character.

The following is a detailed description of my new variety, named "Tipper" (Joltíp) with color terminology in accordance with The Royal Horticultural Society Colour Chart (R.H.S.C.C.). The terminology used in color description herein refers to plate numbers in the aforementioned color chart, e.g. "41D" is plate 41D of The Royal Horticultural Society Colour Chart.

Parentage: Seedling.

*Seed parent.*—"Chris Jolly".

*Pollen parent.*—"Chattem Centennial".

Class: Miniature.

The following observations are made of specimens grown outdoors at Kent County, Md. during the month of August.

2

FLOWER

Blooming habit: Continuous.

A. Bud:
- (1) *Size.*—Medium.
- (2) *Form.*—Exhibition.
- (3) *Color.*—When sepals first divide — 39B; When petals begin to unfurl — 41D; When half blown — 41D; Inside of petals — 38A; On reverse of petals — 41D.
- (4) Sepals.—Same size as bud 2.0 cm.
- (5) Peduncle.—2.5 cm length, Aspect — straight. Strength — medium. Color — 191A.

B. Bloom:
- (1) *Size.*—4.5 cm full blown.
- (2) *Borne.*—Singly.
- (3) *Form.*—High centered, Urn shaped.
- (4) *Petalage.*—34–36.
- (5) *Color.*—During first two days. Center of flower medium pink — 41B, Outer petals — 35B. Base of petals 3C. Reverse of petals — 41D.
- (6) *Color change.*—General tonality from a distance is coral pink. The color lightens slightly overall as bloom ages. Finishes to nera 55C after 4 or more days.

C. Petals:
- (1) *Texture.*—Thick.
- (2) *Appearance.*—Satiny.
- (3) *Form.*—Broad tear shape.
- (4) *Arrangement.*—Regularly arranged shingle-like overlay.
- (5) *Petaloids in center.*—Few.
- (6) *Persistence.*—No detachment noted.
- (7) *Fragrance.*—Mild.
- (8) *Lasting quality.*—5–6 days on plant, 5–8 days as cut flower.

REPRODUCTIVE ORGANS

A. Stamens, anthers: Regularly arranged around styles.
- (1) *Color.*—Yellow, near to 60A.

B. Pollen.—Color is yellow, near to 22A.

C. Styles.—Medium length and even.

D. Stigmas:
- *Color.*—Yellow — 64A.

E. Hips.—Globular, 1.4 cm, green 147C changing to Orange at maturity.

PLANT

A. Form: Upright.

B. Growth: Very vigorous.

*Height attained.*—40 to 45 cm.

C. Foliage: Compound of 5 leaflets.

(1) *Size.*—Medium.

(2) *Quantity.*—Abundant.

(3) *Color.*—New foliage: upper side — 146A, under side — 146B. Old foliage: upper side 137A, under side 147B.

(4) *Shape.*—Oval, pointed.

(5) *Texture.*—Upper side, smooth. Under side — rough.

(6) *Edge.*—Serrated.

(7) *Serration.*—4 per cm.

(8) *Leaf stem.*—Color — 146A; under side — 191A.

(9) *Stipules.*—Short.

D. Wood:

(1) *New wood.*—Color — 147B. Bark — smooth.

(2) *Old wood.*—Color — 137C. Bark — smooth.

E. Thorns:

(1) *Quantity.*—On main stalks from base — very few; on laterals non visible. Form: flat base, bayonnet shaped. Length: medium. Color when young — 22A. Position: irregular.

(2) *Prickles.*—None.

F. Plant's disease resistance:

(1) *Mildew.*—Moderate.

(2) *Blackspot.*—Moderate.

(3) *Rust.*—None observed.

G. Winter hardiness. Good winter hardiness.

I claim:

1. A new and distinct variety of rose plant of the miniature rose class, substantially as shown and described, characterized particularly by clear coral pink well formed blooms that hold their color throughout the life of the flower.

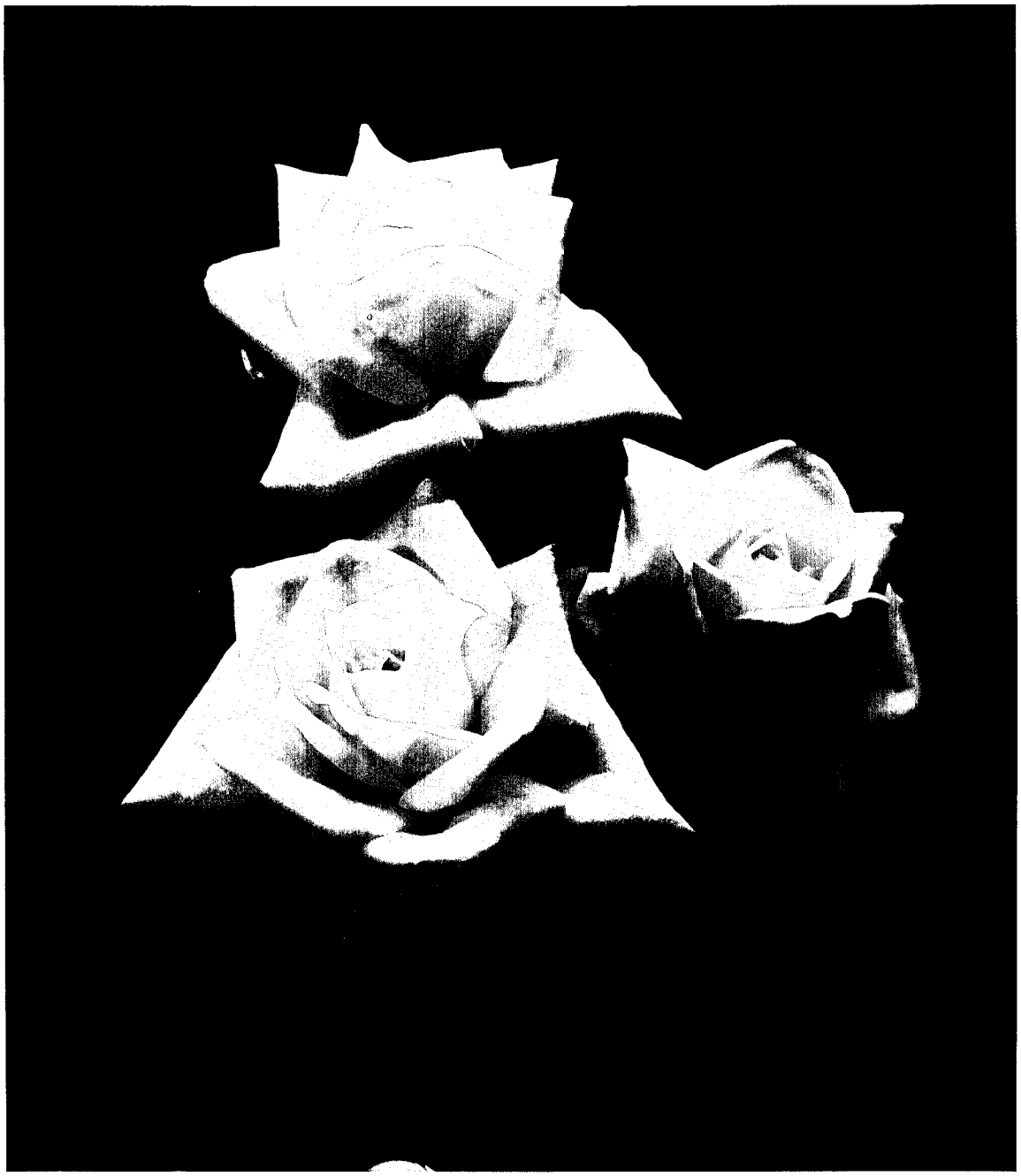

* * * * *